(12) United States Patent
Buus

(10) Patent No.: US 9,549,840 B2
(45) Date of Patent: Jan. 24, 2017

(54) OSTOMY APPLIANCE WITH A RELEASE LINER HAVING A PREDEFINED FOLDING LINE

(75) Inventor: Hasse Buus, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/132,608

(22) PCT Filed: Dec. 15, 2009

(86) PCT No.: PCT/DK2009/050336
§ 371 (c)(1),
(2), (4) Date: Jun. 3, 2011

(87) PCT Pub. No.: WO2010/069326
PCT Pub. Date: Jun. 24, 2010

(65) Prior Publication Data
US 2011/0245789 A1    Oct. 6, 2011

(30) Foreign Application Priority Data
Dec. 18, 2008   (DK) .................................. 2008 01807

(51) Int. Cl.
| A61F 5/44 | (2006.01) |
| A61F 5/449 | (2006.01) |
| A61F 5/445 | (2006.01) |
| A61F 5/443 | (2006.01) |

(52) U.S. Cl.
CPC ............... *A61F 5/445* (2013.01); *A61F 5/443* (2013.01)

(58) Field of Classification Search
USPC .............................................. 604/344; 602/58
See application file for complete search history.

(56) References Cited

U.S. PATENT DOCUMENTS

| 3,081,771 A * | 3/1963 | Lee .......................... A61F 5/443 604/344 |
| 5,384,174 A * | 1/1995 | Ward et al. ................... 428/41.5 |
| 5,916,654 A * | 6/1999 | Phillips ..................... E04D 5/12 428/40.1 |
| 6,248,915 B1 | 6/2001 | Ito et al. |
| 6,332,879 B1 * | 12/2001 | Nielsen .................... A61F 5/443 604/332 |
| 6,814,720 B2 * | 11/2004 | Olsen ....................... A61F 5/448 337/344 |

(Continued)

FOREIGN PATENT DOCUMENTS

| GB | 2225956 A1 | 6/1990 |
| WO | 2010060116 A1 | 5/2010 |

*Primary Examiner* — Adam Marcetich
*Assistant Examiner* — Guy K Townsend
(74) *Attorney, Agent, or Firm* — Coloplast Corp., Coloplast A/S; Nick Baumann

(57) ABSTRACT

An ostomy appliance for attachment to the stoma body comprising an adhesive wafer and a collecting pouch attachable to an adhesive wafer, the wafer comprises a backing layer and a skin-facing adhesive layer, wherein the adhesive skin-facing surface of the wafer is provided with a release liner covering the skin-facing surface of the adhesive layer, the release liner comprising at least a first part and a second part, the first and the second part being interconnected along a predefined folding line and wherein both the first and the second part of the release liner is in contact with the adhesive. The construction facilitates stepwise application.

20 Claims, 2 Drawing Sheets

(56) References Cited

U.S. PATENT DOCUMENTS

| | | | | |
|---|---|---|---|---|
| 6,830,565 B2* | 12/2004 | Cisko, Jr. | ............... | A61F 5/443 |
| | | | | 604/336 |
| 6,894,204 B2* | 5/2005 | Dunshee | ............. | A61F 13/0203 |
| | | | | 602/41 |
| 7,078,582 B2* | 7/2006 | Stebbings | ........... | A61F 13/0256 |
| | | | | 602/54 |
| 7,160,275 B2* | 1/2007 | Falconer | ................ | A61F 5/441 |
| | | | | 604/333 |
| 2002/0187294 A1* | 12/2002 | Zhou | ...................... | A61L 15/58 |
| | | | | 428/40.1 |
| 2003/0125685 A1* | 7/2003 | Swenson | ................. | A61L 15/26 |
| | | | | 604/369 |
| 2003/0171737 A1* | 9/2003 | Leise, Jr. | ................ | A61F 5/448 |
| | | | | 604/540 |
| 2006/0184145 A1 | 8/2006 | Ciok et al. | | |
| 2007/0071971 A1* | 3/2007 | Drogan | .................... | B32B 7/06 |
| | | | | 428/343 |
| 2007/0255240 A1* | 11/2007 | Ciok | ...................... | A61F 5/445 |
| | | | | 604/339 |
| 2007/0260206 A1* | 11/2007 | Mullejans | .............. | A61F 5/445 |
| | | | | 604/332 |

* cited by examiner

OSTOMY APPLIANCE WITH A RELEASE LINER HAVING A PREDEFINED FOLDING LINE

BACKGROUND OF THE INVENTION

1. Field of the Invention

The invention relates to an ostomy appliance for attachment to the body and for collecting bodily waste discharged from a stoma.

Ostomy appliances are usually in the form of a receptacle, e.g. a bag, pouch or for receiving the waste, connected to an adhesive wafer that can be attached to the skin of the patient. The wafer is typically in the form of a backing layer coated on the skin-facing surface with an adhesive layer and the wafer is further provided with an aperture for accommodating the stoma. The size and shape of said aperture can often be adapted individually to fit the anatomy of the patient.

One of the crucial parts of such appliances is the adhesive wafer. The wafer should be able to fit leak proof around the body opening and have good adherence to the skin without unintended detachment from the skin, but at the same time the wafer should be easy to remove again without damaging the skin. Furthermore, the wafer should be able to follow the movements of the body and be comfortable to wear. The components of the wafer, the adhesive and the backing layer determine these properties.

The adhesive of such appliances is usually a hydrocolloid adhesive coated in a relatively thick layer on a backing layer and combined with the fact that this adhesive has a high modulus, the appliance may be inflexible and bulky to wear.

The wafer of an ostomy appliance may be made softer by exchanging the hydrocolloid adhesive with a softer adhesive. However, providing an ostomy appliance with a soft adhesive may give rise to new problems. Whereas the conventional hydrocolloid adhesive wafer was rather stiff and thereby easy to handle and apply, the soft adhesive wafers are soft and mechanical unstable and may easily fold and stick to itself during application.

When applying an adhesive wafer around a stoma the conventional hydrocolloid adhesive wafers are relatively stable and easy to handle, even when the release liner is removed prior to application. The construction of the current hydrocolloid adhesives in modern stoma care products are carried out in such a manner that the wafer, when the release liner is removed, is stiff enough in order for the product to stay in an almost planar manner. In other words the product does not bend, curl or fold significantly during application.

This is due to the choice of backing layer and adhesive. The backing layer is usually a relatively stiff polymer backing and the adhesive is a polymer based continuous phase filled with particles that add to the modulus of the adhesive. The combination of a high modulus backing and adhesive makes the adhesive wafer very stiff.

Due to the choice of backing layer, a relatively stiff polymer backing layer stabilizes the product in combination with a hydrocolloid adhesive. The presence of an absorbent filler, such as hydrocolloid particles, makes the adhesive stiffer. A polymeric matrix for the adhesive comprising PIB (polyisobutylene), SIS (styrene isoprene styrene block copolymer), resin etc. produces a relatively stiff adhesive.

When the type of adhesive is changed from the highly filled relatively stiff materials to a soft, low or non filled adhesive, the need for a soft backing layer is essential in order to obtain the right properties for the intended use. This makes the adhesive wafer very soft, flexible and unable to hold itself in a relatively planar manner after removal of the release liner. The adhesive wafer itself is so flexible that the side portions of the wafer will bend down with gravity after removal of release liner, resulting in the adhesive to stick to itself, bend, curl or fold and the wafer will be useless.

When placing the ostomy appliance around the stoma the usual procedure is to first adjust and attach the bottom part of the appliance to the abdominal area below the stoma, and afterwards attach the upper part of the appliance.

For soft adhesives removing the entire release liner prior to application makes it difficult to control the adhesive and get it applied in the right position on the abdominal skin without introducing fold or tensions in the adhesive that subsequently could lead to leakage of effluents under the adhesive.

2. Description of the Related Art

Handling soft and/or thin adhesive wafers may be addressed in different ways. The adhesive surface may be covered with a number of release liners or the backing layer may be provided with detachable support means.

The wafer may be provided with two release liners, each covering an area of the product. Hereby, the user can remove one release liner, attach the exposed adhesive surface to the body and then remove the second liner and apply the rest of the wafer, all the way through without touching the adhesive surface with the fingers. This solution is for hygiene purpose and is often referred to a non-touch solution.

Devices for faecal management often comprise two or more release liners in order to ease the application to the curved and complicated perianal area. This has been made to facilitate the fact that the adhesive wafer has to be bent approximately 180 degrees in order to adhere to the buttocks.

Today, conventional ostomy appliances are provided with a single release liner, covering the entire adhesive surface. A non-touch solution is achieved by having a non-adhesive tab or ear on the edge portion of the flange for holding during application without touching the adhesive. The tab or ear may be used to ease detachment of the wafer later. This solution is suited for mechanical stable wafers while soft wafers comprising soft adhesive would be difficult—not to say impossible—to handle with such release liner system.

Thus, there is still a need for an ostomy appliance having a high flexibility and comfort for the user and being easy to apply.

SUMMARY OF THE INVENTION

One object of the present invention is to provide an ostomy appliance with a release liner that facilitates easy and stepwise application of the adhesive wafer.

BRIEF DESCRIPTION OF THE DRAWINGS

The invention is disclosed more in detail with reference to the drawings in which.

DETAILED DESCRIPTION OF THE PRESENT INVENTION

Figure 1:
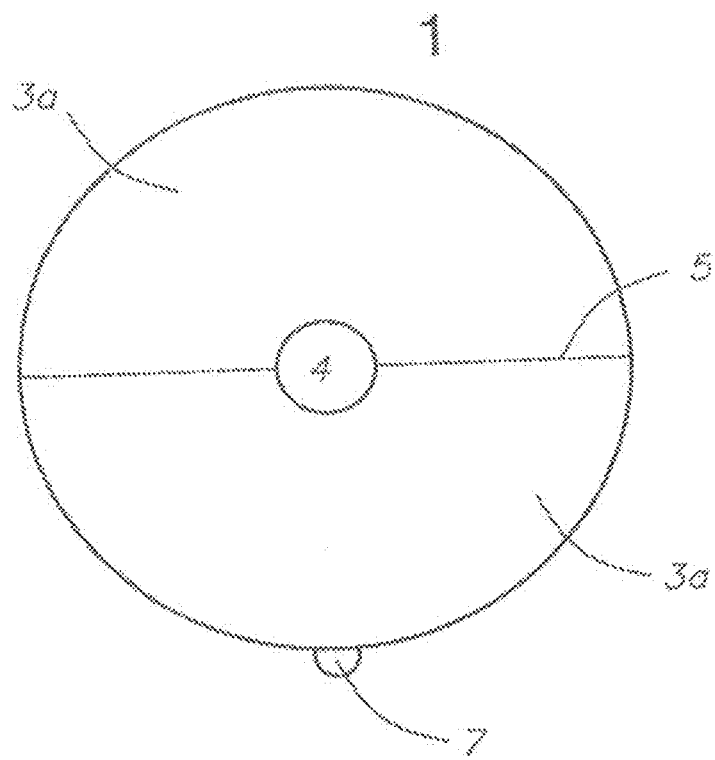
FIG. 1 shows a preferred embodiment of the invention seen from below.

The invention relates to an ostomy appliance for attachment to the stoma body comprising an adhesive wafer and a collecting pouch attachable to an adhesive wafer, the wafer comprises a backing layer and a skin-facing adhesive layer, wherein the adhesive skin-facing surface of the wafer is provided with a release liner covering the skin-facing surface of the adhesive layer, the release liner comprising at least a first part and a second part, the first and the second part being interconnected inseparably along a predefined folding line and wherein both the first and the second part of the release liner is in contact with the adhesive.

The first and the second part are in-separately interconnected, to be understood as that they cannot be separated from each other's without damaging the release liner. Preferably, the first and the second part are parts of the same sheet.

The adhesive layer of the wafer may be a soft adhesive having a tensile strength at 20% strain of less than 0.75N for a wafer sample having a width of 4 mm.

By predefined folding line is meant a line in the release liner where the release liner will bend sharply when it is folded. A release liner being bended without such folding line will bend to form an arch in the bended area, not an angle.

When the first part and the second part of the release liner is bent towards each others, by releasing one of the parts from the adhesive surface, an angle is formed along the predefined folding line.

It is preferred that the folding line extends from one edge portion of the wafer to another edge portion of the wafer, and the folding line being linear. By linear is meant a straight line.

Before application, the entire release liner is attached to the adhesive surface of the wafer; the release liner has a substantially flat configuration, following the configuration of the skin-facing surface of the wafer.

The soft and flexible collecting device according to the invention requires a solution for proper handling during application of the device to the skin, because the handling of a soft and flexible adhesive wafers during application is very difficult as it will bend and cannot stay in a planar position without support. By providing the release liner with a predefined folding line, the wafer can now be applied stepwise, using only one release liner. The first part of the release liner is detached from the adhesive surface and bended over to fully or partly overlap the second part of the release liner. The predefined folding line facilitates the first and the second part of the release liner will be connected by the folding line by a a sharp angle, thereby facilitating that the two release liner parts lying substantially parallel to each other. Hereby the wafer, with folded release liner, will assume a substantially flat/planar configuration. The exposed adhesive surface is then applied to the body, thereby bonding the adhesive wafer partially to the skin. Then the unattached release liner part is then removed by displacing the release liner in a direction transverse to the folding line and attaching the remaining adhesive surface of the wafer to the skin. The flat configuration of the wafer with bended release liner facilitates more easy and precise application as the wafer can be brought closer to the application site. A wafer with a bended release liner without folding line will form an arch and be more bulky.

Furthermore, the point or line where the release liner detaches from the adhesive when the release liner is bent will be more distinct when the release liner bends in an angle, due to the predetermined folding line, thereby facilitating more precise application.

Thus, the predefined folding line of release liner of the appliance according to the invention renders it possible for the user to apply a very soft and flexible adhesive wafer to the skin in an uncomplicated way. The release liner can be removed stepwise during the application of the wafer thereby facilitating easy and safe application to the peristomal skin without the risk of touching the adhesive surface.

The size of the angle being formed when the release liner is bent depends on the character of the folding line as well as the properties of the release liner. It is preferred that the angle between the first and the second part is less than 90 degrees, more preferred less than 45 degrees when the first and the second part of the release liner are superimposed.

It has been found that by introducing a predefined folding line, where the release liner will naturally fold and bend down when separated from the adhesive thereby exposing a part of the adhesive surface, an easier and more precise application of the ostomy appliance is achieved. It is then possible to the user in a controlled manner to position and attach the exposed part of the adhesive to the skin, and afterwards remove the last part of the release liner. The application can be done stepwise, providing more control for the user.

The release liner may comprise multiple folding lines. Preferably the release liner only contains one folding line.

In one embodiment of the invention the release liner is provided with two folding lines. The folding lines may be substantially parallel in order to achieve stepwise application. The part of the release liner being situated between may be straight or folded.

The folding lines may be arranged substantially perpendicular to each others, thus opening up for the user to choose the preferred direction of application. The folding lines may cross each others in any desired angle, e.g. the angle between the folding lines defining a 45 degrees angle.

The release liner is typically in the form of a sheet having a uniform thickness.

The folding lines may be a weakened line where the material is thinner and/or softer than the rest of the release liner, thereby facilitating that the release liner will make a natural angle along the predetermined line when a part of the release liner is separated from the adhesive surface of the wafer.

In one embodiment of the invention the folding line is in the form of a line with reduced thickness. Such line may be produced by cutting partly through the release liner or by applying heat and/or pressure along the folding line to produce a depression in the liner. The thickness of the release liner along this line will thus be smaller than the overall thickness of the release liner.

The first and the second part of the release liner are inseparable, meaning that the cohesion between the first and the second part of the release liner along the folding line should be strong enough to avoid the first and the second part of the release liner being ripped apart along the folding line during handling and removal of the release liner from the dressing.

The folding line may be less than 75%, 60%, 50%, 40% or 30% of the overall thickness of the release liner.

The folding lines can be a uniform line with deviation in thickness compared to the rest of the release liner, or it may be in the form of a number of spaced smaller lines or points, forming a perforated line.

The folding lines or pattern can be produced by an impression roll or it can be a cut into the release line.

The folding line is produced in the release liner either prior to or after the attachment of the adhesive wafer.

The folding lines are preferably made on the surface of the release liner facing away from the adhesive surface, thereby facilitating that the adhesive surface will remain flat and smooth during production or storage.

The folding line may be made by application of pressure and/or the folding line may be made by treatment with heat.

Preferably, the folding line is extending through the central portion of the wafer.

By the phrase "central portion" is meant an area at the central portion of the wafer. Central should be interpreted as being in the middle portion of the wafer and not peripheral, but should not necessarily be symmetrically located on the wafer. The central portion of the wafer may be provided with an aperture for accommodating the stoma. The folding line may preferably cross the aperture.

In another embodiment the line does not run through the centre, in this case it is preferred to have a folding line in both the upper and lower part of the wafer in such an order that the it is possible to fold and afterwards remove the folded part of the release liner from either above or underneath, depending on the preference of the end-user, without intersecting the stoma.

The folding line may have any orientation across the wafer but it is preferably substantially horizontal or vertical. The orientation should be understood relative to a wafer applied to an upright standing user.

The release liner may be provided with at least one ear extending beyond the adhesive surface. By ear is meant a tab member, adapted for gripping with the fingers, serving as a handle when the release liner is detached from the adhesive surface of the wafer. In one embodiment of the invention the release liner is provided with two ears extending beyond the adhesive surface, positioned on opposing edges thereof. Hereby the user is free to choose from which direction the release liner should be detached and application of the wafer begins.

The release liner of the appliance of the present invention is preferably in the form of a polymer film, foil or paper, having release properties that enable the adhesive to be released easily from the liner. Such properties may be inherent in the material or the layer may be siliconised or coated with a low surface tension coating. Release liners are in general made on a mechanically stiff backing such as paper, polyethylene, polypropylene or polyethylene terephthalate, this stiffness will support the adhesive wafer when applying the collecting device.

The release liner should have sufficient stiffness to stabilize and ease the handling of the soft wafer. However, after attaching the first exposed part of the adhesive to the abdominal skin, too much stiffness will jeopardize the removal of the second (folded) part of the release liner. A preferred release liner is made from polypropylene and poly(ethylene terphthalate) with a thickness of 50-150 microns.

Handling of a very soft adhesive wafer for an ostomy appliance is eased by the present invention that allows the user to remove the release liner gradually while applying the ostomy appliance.

The ostomy appliance of the present invention comprises an adhesive wafer comprising a thin elastic, low modulus backing layer covered with a soft absorbing adhesive on one surface. The adhesive layer may be in the form of one or more layers.

By soft adhesive wafer, we mean an adhesive wafer with a tensile strength at 20% strain of less than 0.75N for a wafer sample having a width of 4 mm using the method disclosed herein.

In a preferred embodiment of the invention, the wafer has a tensile strength at 20% strain of less than 0.5N for a wafer sample having a width of 4 mm using the method disclosed herein.

By virtue of the fact that the adhesive layer of the ostomy appliance of the present invention is very soft, it can adhere to irregularities in the skin in a way that fluid cannot leak underneath the adhesive wafer. The ostomy appliance according to the invention is also very shapeable, which means that the edge of the opening in the component can be applied very close to a stoma without risk of irritation, strangulation or bleeding of the mucous membrane at the base of the stoma.

The adhesive wafer of the ostomy appliance according to the invention can be stretched together with the skin in a way that there is considerably less risk of shearing between skin and adhesive, which shearing can give rise to mechanical damage to the skin and unintended detachment of the ostomy appliance.

The backing layer of the ostomy appliance of the present invention is preferably in the form of a polymer film, coating, laminate, textile or non-woven. The backing layer is preferably a highly flexible film being strong enough for attachment of e.g. couplings and/or pouch and for removing the ostomy appliance in one piece, but soft enough to follow the movements of the body. A preferred backing layer is a polyurethane film.

Preferably, the backing layer has thermoplastic elements that enable welding of e.g. a pouch or coupling ring to the adhesive wafer. Preferred thickness of the backing layer is between 15-60 μm in order to maintain the softness of the adhesive wafer.

The adhesive of the appliance according to the present invention has a G* at 0.01 Hz less than 15,000 Pa, preferably less than 7,500 Pa as measured using the technique enclosed herein. This means that the adhesive is considerably softer than conventional adhesive systems used for attaching collecting devices to skin. Such an adhesive is soft and the produced wafer will tend to collapse under its own weight.

It is preferred that the entire skin-facing surface of the backing layer is coated with the soft adhesive. Hereby, a soft wafer is achieved. In one embodiment of the invention, the soft adhesive may only cover the peripheral part or the central part oft the wafer. Such a wafer may have 10-90% of total area covered by the soft adhesive system and the rest covered by conventional ostomy type adhesives.

Examples of soft adhesives may be adhesives based on silicone, polyurethane or acrylate.

As used herein a cross-link means a small region in a macromolecule (polymer chain structure) from which more than 2 chains emanate.

In a preferred embodiment of the invention, the adhesive comprises ethylene vinyl acetate. The adhesive comprising ethylene vinyl acetate may suitably be an adhesive known in the art such as the adhesive composition disclosed, for example in International Patent Application No. PCT/DK2008/050146.

In a preferred embodiment of the invention the adhesive layer of the ostomy appliance of the invention may comprise a polyalkyleneoxide polymer and an organosiloxane based cross-linked adhesive system.

According to one embodiment of the invention the adhesive layer of the ostomy appliance may comprise the reaction product of:
    (i) a polyalkyleneoxide polymer having one or more unsaturated end groups and (ii) an organosiloxane comprising one or more Si—H groups, carried out in the presence of an addition reaction catalyst.

According to another embodiment of the invention the adhesive composition of the ostomy appliance comprises more than 90% w/w of the polyalkylene oxide polymer that consists of polymerised alkyleneoxide moities having three or more carbon atoms.

According to another embodiment of the invention, the adhesive composition of the ostomy appliance comprises the reaction product of:

(i) a polyalkyleneoxide polymer having at least two unsaturated end groups and wherein more than 90% w/w of the polyalkylene oxide polymer consists of polymerised alkyleneoxide moities having three or more carbon atoms, (ii) a polysiloxane cross-linking agent comprising 3 or more Si—H groups and optionally (iii) a polysiloxane chain extender comprising up to 2 Si—H groups carried out in the presence of an addition reaction catalyst.

According to a preferred embodiment of the invention, the addition reaction catalyst is a Pt vinyl siloxane complex.

According to a preferred embodiment of the invention, the polyalkylene oxide polymer is polypropyleneoxide.

According to a further preferred embodiment of the invention, the weight percent of polyalkylene oxide in said reaction product is 60% or above.

The polyalkylene oxide polymer having one or more unsaturated groups may be branched or linear.

However, suitably, the polyalkylene oxide polymer is linear and has two unsaturated end groups.

In one particular embodiment of the invention the polyalkylene oxide polymer is polypropyleneoxide.

The polypropylene oxide having unsaturated end groups may be a compound of Formula

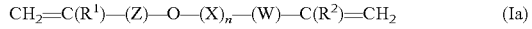     (Ia)

or

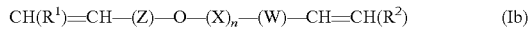     (Ib)

wherein $R^1$ and $R^2$ are independently selected from hydrogen and $C_{1-6}$-alkyl;

Z and W is $C_{1-4}$-alkylene;

X is —$(CH_2)_3$—O— or —$CH_2$—$CH(CH_3)$—O—; and n is 1-900, more preferred 10-600, or most preferred 20-600.

The number average molecular weight of the polyalkylene oxide having unsaturated end groups is suitably between 500 and 100,000, more preferred between 500 and 50,000 and most preferred between 1,000 and 35,000.

Polypropylene oxide having unsaturated end groups may be prepared as described in U.S. Pat. No. 6,248,915 and WO No. 05/032401 or analogously to the methods described therein. Other polyalkylene oxide polymers may be prepared analogously.

The polysiloxane cross-linking agent comprising 3 or more Si-H groups is suitable a compound having the formula

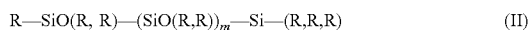     (II)

wherein at least three of the groups R are hydrogen and the rest of the groups R are each independently selected from $C_{1-12}$-alkyl, $C_{3-8}$-cycloalkyl, $C_{6-14}$-aryl, and $C_{7-12}$-arylalkyl; and m is 5-50, or preferably 10-40. The number average molecular weight as determined by GPC is suitably 500-3,000.

One or more cross-linking agents of formula (II) may be used in the cross-linking reaction.

In one embodiment of the invention, a mixture of one or more cross-linking agents of formula (II) comprising 3 or more Si—H groups and a polysiloxane chain extender comprising up to 2 Si—H groups is used in the cross-linking reaction.

The polysiloxane chain extender is suitably a compound having the formula

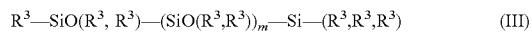     (III)

wherein up to 2 of the groups $R^3$ are hydrogen and the rest of the groups $R^3$ are each independently selected from $C_{1-12}$-alkyl, $C_{3-8}$-cycloalkyl, $C_{6-14}$-aryl, and $C_{7-12}$-arylalkyl; and m is 0-50. The number average molecular weight as determined by GPC is suitably between 200 and 65,000, most preferably between 200 and 17,500.

As used herein $C_{1-12}$-alkyl means a linear or branched alkyl group having 1 to 12 carbon atoms, $C_{1-8}$-alkyl means a linear or branched alkyl group having 1 to 8 carbon atoms, and $C_{1-6}$-alkyl means a linear or branched alkyl group having 1 to 6 carbon atoms, such as methyl, ethyl, propyl, isopropyl, butyl, pentyl and hexyl.

As used herein $C_{1-4}$-alkylene means a linear or branched divalent alkylene group having 1 to 4 carbon atoms, such as methylene, ethylene, propylene, isopropylene, butylenes and isobutylene.

As used herein $C_{3-8}$-cycloalkyl means a cyclic alkyl group having 3-8 carbon atoms, such as cyclopentyl and cyclohexyl.

As used herein $C_{6-14}$-aryl means a phenyl or naphthyl group optionally substituted with $C_{1-6}$-alkyl, such as tolyl and xylyl.

As used herein $C_{7-12}$-arylalkyl means aryl attached to a $C_{1-6}$-alkyl group, where $C_{1-6}$-alkyl and aryl is as defined above, such as benzyl, phenethyl and o-methylphenethyl.

In the compound of formula (II) and in the compound of formula (III), the groups R and $R^3$, which are not hydrogen, are suitably each independently selected from a member of the group $C_{1-6}$-alkyl, $C_{6-14}$-aryl or $C_{7-12}$-arylalkyl.

The Si—H groups may be situated at either end of the compound of formula (II). However, at least one Si—H group is preferably positioned within the —$(SiO(R^3, R^3))_m$— chain of the compound of formula (II).

The polysiloxane cross-linking agent and the chain extender may be prepared as described in Japanese Patent Application No. 2002-224706 and WO No. 05/032401 or analogously to the methods described therein.

An addition reaction is, in its simplest terms, a chemical reaction in which the atoms of an element or compound react with a double bond or triple bond in an organic compound by opening up one of the bonds and becoming attached to it, forming one larger compound. Addition reactions are limited to chemical compounds that have multiple-bonded atoms. Hydrosilylation is an addition reaction between, for example, a carbon-carbon double bond in a compound and a reactive hydrogen from a hydrogen siloxane.

Suitable addition reaction catalysts are any hydrosilylation catalysts, preferably platinum (Pt) catalysts. Pt-catalysts for the first part of the two-component sealant are described in U.S. Pat. No. 6,248,915. In consideration of toxicity potential, Pt complex catalyst where Pt is at a valency state of zero is preferred. Preferred catalysts are platinum-vinylsiloxanes and platinum-olefin complexes, such as Pt-divinyl tetramethyl disiloxane.

The reaction is suitably carried out neat at a temperature between 25° C. and 150° C. It is not necessary to use a solvent for the reaction, which is an advantage for any adhesive, but especially for skin applications.

Suitably, the ratio of the number of reactive Si—H groups in the polysiloxane cross-linking agent to the number of unsaturated groups in the polypropylene oxide, which are reactive with Si—H groups under the reaction conditions, is between 0.2 and 1.0.

The amount of polysiloxane used for the cross-linking is suitably less than 15% w/w and more preferred below 10% w/w of the amount of polyalkylene oxide polymer having unsaturated end groups.

The cross-linking reaction does not lead to complete cross-linking of all the polyalkylene oxide polymers. The adhesive comprises a mixture of cross-linked and non cross-linked polyalkylene oxide polymer.

The adhesive composition of the ostomy appliance according to the invention may contain other conventional ingredients for adhesive compositions, such as tackifiers, extenders, non-reactive polymers, oils (e.g. polypropylenoxide, ethyleneoxide-propyleneoxide copolymers, mineral oil), plastizisers, fillers, and surfactants. The adhesive may also comprise pharmaceutically active ingredients. These optional ingredients may be present in the reaction mixture during the cross linking reaction.

It may be advantageous that the soft adhesive comprises absorbent particles. The particles may be absorbent articles such as mineral salt, hydrocolloid, microcolloids or super absorbers in order for the adhesive to absorb moisture from skin.

Microcolloid particles are well known in the art e.g. from International Patent Application No. WO 02/066087, which discloses adhesive compositions comprising microcolloid particles. The microcolloid particles may have a particle size of less than 20 microns.

The collecting pouch may be detachable from the adhesive wafer by a coupling system or the pouch and the wafer may be integrated with the wafer, e.g. by welding. The two versions are known as one piece or two-piece appliances for ostomy.

The wafer of the device of the invention may have different shapes, such as circular, oval, square or user defined shape and the same applies for the attachment zone as well as the aperture.

In order to avoid rolling up of the edge portion during wear, it may be advantageous to bevel the edge portion of the wafer.

DESCRIPTION OF THE PREFERRED EMBODIMENTS

The invention is now explained more in detail with reference to the drawings showing preferred embodiments of the invention.

FIG. 1 shows a wafer of an ostomy appliance according to the invention. The wafer is shown from the skin-facing side. For clarity, the wafer is shown without attached coupling means or collection pouch mounted in the non-skin-facing surface of the wafer.

In FIG. 1 is shown a wafer with a central aperture (4) for receiving a stoma, the adhesive surface of the wafer being covered with a release liner comprising a first part (3*a*) and a second part (3*b*), the first and the second part being joined along a predefined folding line (5), extending across the middle portion of the adhesive wafer. The release liner can optionally be provided with an ear (7) for easy detachment from the adhesive surface.

Figure 2:
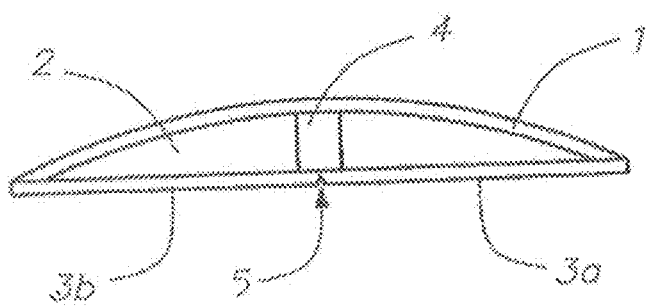
FIG. 2 shows the embodiment of the invention in cross-section.

The same embodiment of the invention is shown in cross-section in FIG. 2, where the adhesive wafer comprises an adhesive layer (2) covered on the non-skin-facing surface by a backing layer (1). The release liner (3*a*, 3*b*) is provided with a folding line (5) in the form of a depression.

Figure 3:
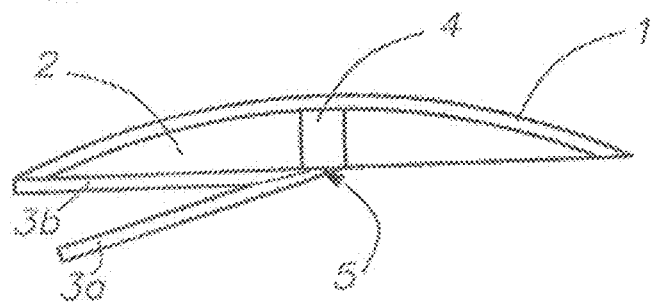
FIG. 3 shows the embodiment of the invention, prepared for application

When the wafer is to be applied to the peristomal skin of a user, the first part (3*a*) of the release liner is detached from the adhesive surface, e.g. by grapping the ear (7), and the first part is superimposed over the second part (3*b*), see FIG. 3. Due to the presence of the predefined folding line (5), the release liner will bend to form a sharp angle along the folding line (5). The configuration of the wafer with folded release liner is generally flat thereby facilitating that the wafer can be brought close and more parallel to the skin during application, hereby easing a precise application. Furthermore, the folding line serves as a natural stop for detachment of the release liner thus avoiding that a too large part of the adhesive surface may be exposed, thereby rendering the handling of the wafer difficult.

Figure 4:
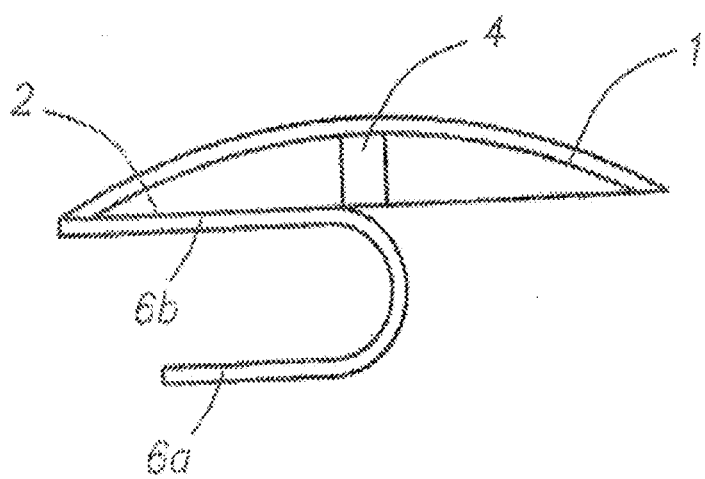
FIG. 4 shows a prior art wafer prepared for application.

In FIG. 4 is shown a prior art wafer, without the folding line. When the first part (6*a*) of the release liner is folded to superimpose the second part (6*b*) of the release liner the interconnection of the two parts (6*a*, 6*b*) will form an arch or a sector of a circle, rendering it difficult to bring the wafer close and parallel to the skin during application.

Materials and Methods

Determination of Mechanical Properties of Adhesive Wafer

For measuring softness of the wafer, the testing guidelines from standard ISO527-1 were used. However, the parameters defined in ISO527-1 are in it self not sufficient to describe the relevant parameters for ostomy devices exactly. An ostomy device is placed on the stomach, on skin that can easily deform more than 20%. The relevant deformation for a soft adhesive wafer is in the same magnitude and we have therefore defined softness (modulus) of adhesive wafer as the force in Newton at 20% deformation divided by initial sample width. We used 'dog-bone' test specimens similar to the ones described in ISO 527-2 FIG. 1, but with different dimensions to accommodate the fact that some adhesive wafers are too small to be tested with ISO 527-1. We used test samples that corresponded with the samples from ISO527.2 FIG. 1, but where the width $b_1$ of the narrow portion was 4 mm and Gauge length $L_0$ was 10 mm. Relative deformation £ was calculated as the absolute deformation $\Delta L$ divided by the initial length $L_0$ as described in ISO 527-1. The rate of deformation was set to 1 mm/s. To accommodate the fact that some layers are isotropic, samples were measured in the softest direction. The obtained values are averages of at least 3 measurements.

Determination of G*.

The parameter G* or complex modulus as defined in "Dynamics of polymeric liquids", Vol. 1, sec. ed. 1987, Bird, Armstrong and Hassager, John Wiley and Sons inc., was used as a measure of the hardness/softness of an adhesive. G* at 32° C. and 0.01 Hz was measured as follows: A plate of un-foamed adhesive material was pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurement was carried out at 32° C. To avoid any confusion, note that G* in here means the absolute value of the complex G*.

The invention claimed is:

1. An ostomy appliance for attachment to a stoma body comprising an adhesive wafer configured to be attached to a collection pouch, the adhesive wafer including a backing layer and a skin-facing adhesive layer, a skin-contacting surface of the skin-facing adhesive layer being provided with a one-piece release liner covering the skin-contacting surface of the skin-facing adhesive layer, the one-piece release liner having a first part inseparably connected to a second part by a predefined folding line between the first part and the second part, the predefined folding line having a depression, the first part and the second part each having a first designated thickness, and the predefined folding line having a second designated thickness that is less than the first designated thickness prior to the first part and the second part being situated to at least partially face each other, such that material of the one-piece release liner has a cut out in the depression extending partly through the release liner at and along the predefined folding line, configured to be provided prior to the first part and the second part being detached or removed from the skin-facing adhesive layer, such that the opposite side of first part and the second part from the skin-facing adhesive layer contacting surface are configured to at least partially face each other upon the detachment or removal, the one-piece release liner configured to be folded along the predefined folding line at the cut out in the depression and detached or removed as a single sheet prior to application of the adhesive wafer to the skin around the stoma body via the skin-contacting surface of the skin-facing adhesive layer, an entire surface of the skin-contacting surface of the skin-facing adhesive layer configured to be in direct contact with the one-piece release liner prior to said detachment or removal.

2. The ostomy appliance according to claim 1, wherein an adhesive of the skin-facing adhesive layer has a tensile strength at 20% strain of less than 0.75N for a wafer sample having a width of 4 mm.

3. The ostomy appliance according to claim 1, wherein the predefined folding line further comprises a weakened line.

4. The ostomy appliance according to claim 1, wherein the predefined folding line extends from one edge portion of the adhesive wafer to another edge portion of the adhesive wafer.

5. The ostomy appliance according to claim 1, wherein the predefined folding line is linear.

6. The ostomy appliance according to claim 1, wherein the first designated thickness and the second designated thickness is measured between a surface of the one-piece release liner contacting the skin-contacting surface of the skin-facing adhesive layer and a surface opposite the surface of the one-piece release liner contacting the skin-contacting surface of the skin-facing adhesive layer.

7. The ostomy appliance according to claim 6, wherein the second designated thickness is less than 80% of the thickness of the first designated thickness.

8. The ostomy appliance according to claim 1, wherein the predefined folding line extends through a central portion of the one-piece release liner.

9. The ostomy appliance according to claim 1, wherein when the first part is released from the skin-contacting surface and folded along the predefined folding line and superimposed over the second part, the first part of the one-piece release liner forms an acute angle relative to the second part of the one-piece release liner at the predefined folding line.

10. The ostomy appliance according to claim 1, wherein the one-piece release liner is provided with at least one ear extended beyond an edge of the skin-contacting surface of the adhesive wafer.

11. The ostomy appliance according to claim 1, wherein the one-piece release liner is provided with two ears extending beyond edges of the skin-contacting surface, positioned on opposing edges thereof.

12. The ostomy appliance according to claim 1, wherein a connection between the first part and the second part does not allow separation of the first part from the second part without damaging the one-piece release liner.

13. An ostomy appliance for attachment to a stoma body comprising an adhesive wafer configured to be attached to a collection pouch, the wafer including a backing layer and a skin-facing adhesive layer, a skin contacting surface of the skin-facing adhesive layer being provided with a release liner covering the skin-contacting surface of the adhesive layer, the release liner having a planar surface that includes a predefined folding line such that the release liner is configured to lay flat with the planar surface on a flat surface, the release liner having at least a first part, a second part, and the predefined folding line between the first part and the second part, the predefined folding line having a depression having a second thickness that is less than a first thickness of the first part and the second part, prior to the first part and the second part being situated to at least partially face each other, where the material of the release liner has a cut out in the depression extending partly through the release liner at and along the predefined folding line to provide the second thickness less than the first thickness, the first part being inseparably connected to the second part by the predefined folding line with separation of the first part from the second part not being possible without damage to the release liner, the release liner being a single flat sheet on the skin-contacting surface of the skin-facing adhesive layer prior to being removed, the release liner being sharply folded along the predefined folding line to provide a tab as the first part or the second part configured for detachment or removal of the release liner from the skin-facing adhesive layer.

14. The ostomy appliance according to claim 13, wherein the predefined folding line is a weakened line.

15. The ostomy appliance according to claim 13, wherein the predefined folding line extends from one edge portion of the wafer to another edge portion of the wafer.

16. The ostomy appliance according to claim 13, wherein the predefined folding line is linear.

17. An ostomy appliance for attachment to a stoma body including an adhesive wafer configured to be attached to a collection pouch, the adhesive wafer including:
  a backing layer and a skin-facing adhesive layer, the skin-facing adhesive layer including a skin-contacting surface; and
  a removable release liner covering the skin-contacting surface of the adhesive layer, the release liner including:
    a first side and a second side opposite the first side, the first side and the second side being in contact with the skin-contacting surface of adhesive layer prior to removal of the release liner from the skin-contacting surface of the skin-facing adhesive layer; and
    a weakened line connecting a first part of the release liner to a second part of the release liner and extending from a first edge of the release liner to a second edge of the release liner opposite the first edge, the second side of the release liner including a cut out having a width and extending partly through the release liner at and along a portion of the weakened line, the release liner configured to have a second thickness along the cut out less than a first thickness of the first part and of the second part prior to detachment or removal of the first part or the second part from the skin-contacting surface of the skin-facing adhesive layer, such that the opposite side of first part and the second part from the skin-facing adhesive layer contacting surface are configured to at least partially face each other after the detachment or the removal between the first edge of the release liner and the second edge of the release liner and the cut out configured to provide a stop location on the release liner along the weakened line for the detachment or removal of the first part or the second part from the skin-contacting surface of the skin-facing adhesive layer;

wherein the release liner is configured as a single flat sheet on the skin-contacting surface of the skin-facing adhesive layer prior to being removed, where both the first part and the second part are configured to be in contact with the skin-contacting surface of the skin-facing adhesive layer prior to detachment or removal of the release liner from the skin-facing layer, and wherein the release liner is configured to be folded at and along the weakened line and the cutout when the first part or the second part is detached from the skin-contacting surface of the skin-facing adhesive layer.

18. The ostomy appliance according to claim 1, wherein the folding line is a linear v-shaped predefined folding depression that extends from one edge portion of the adhesive wafer to another edge portion of the adhesive wafer.

19. The ostomy appliance according to claim 18, wherein the linear v-shaped folding line extends through a central portion of the one-piece release liner.

20. An ostomy appliance for attachment to a stoma body comprising an adhesive wafer configured to be attached to a collection pouch, the adhesive wafer including a backing layer and a skin-facing adhesive layer, a skin-contacting surface of the skin-facing adhesive layer being provided with a release liner configured to cover the skin-contacting surface of the skin-facing adhesive layer prior to detachment of the release liner from the skin-facing adhesive layer, the release liner having a planar surface that includes a predefined folding line such that the release liner is configured to lay flat with the planar surface on a flat surface, the release liner having at least a first part inseparably connected to a second part by the predefined folding line having a cut out extending partly through the release liner at and along the predefined folding line, the first part and the second part each having a first designated thickness and the predefined folding line having a second designated thickness that is less than the first designated thickness prior to folding the release liner at the predefined folding line, the release liner configured to be folded along the predefined folding depression and removed as a single sheet during application of the adhesive wafer, an entire surface of the skin-contacting surface of the skin-facing adhesive layer configured to be in direct contact with the release liner prior to detachment or removal of the first part or the second part of the release liner from the skin-facing adhesive layer.

\* \* \* \* \*